US008500442B2

(12) United States Patent (10) Patent No.: US 8,500,442 B2
Knittel et al. (45) Date of Patent: Aug. 6, 2013

(54) COMBUSTION GAS ANALYSIS

(75) Inventors: Trevor S. Knittel, Houston, TX (US); Jie Zhu, Pearland, TX (US); Alan I. Cowie, Friendswood, TX (US); Donald L. Wyatt, Friendswood, TX (US)

(73) Assignee: Yokogawa Corp. of America, Newnan, GA (US)

( * ) Notice: Subject to any disclaimer, the term of this patent is extended or adjusted under 35 U.S.C. 154(b) by 876 days.

(21) Appl. No.: 12/583,765

(22) Filed: Aug. 25, 2009

(65) Prior Publication Data

US 2010/0028819 A1 Feb. 4, 2010

Related U.S. Application Data

(63) Continuation of application No. PCT/US2008/002364, filed on Feb. 22, 2008.

(60) Provisional application No. 60/903,495, filed on Feb. 26, 2007.

(51) Int. Cl.
*F23N 5/26* (2006.01)
(52) U.S. Cl.
USPC ............... 431/76; 431/12; 431/75; 356/437; 73/23.31
(58) Field of Classification Search
USPC ............... 431/76, 75, 12; 356/437; 73/23.31
See application file for complete search history.

(56) References Cited

U.S. PATENT DOCUMENTS

| | | | | |
|---|---|---|---|---|
| 3,831,030 | A | * | 8/1974 | Wrobel et al. ............ 250/339.13 |
| 4,423,487 | A | * | 12/1983 | Buckenham et al. ......... 702/182 |
| 5,252,060 | A | * | 10/1993 | McKinnon et al. ............. 431/12 |
| 6,150,661 | A | * | 11/2000 | McCaul et al. ............... 250/343 |
| 7,217,121 | B2 | | 5/2007 | Thomson et al. |
| 7,244,936 | B2 | | 7/2007 | Von Drasek |
| 7,248,755 | B2 | | 7/2007 | Sappey et al. |
| 2004/0191712 | A1 | | 9/2004 | Thomson et al. |
| 2005/0200475 | A1 | | 9/2005 | Chen |
| 2008/0123712 | A1 | * | 5/2008 | Zhou et al. ...................... 372/55 |

FOREIGN PATENT DOCUMENTS

| WO | WO 2004/090496 | 10/2004 |
|---|---|---|
| WO | WO2004/090496 A2 | 10/2004 |
| WO | WO 2006/104796 | 10/2006 |

OTHER PUBLICATIONS

PCT International Search Report and Written Opinion of the Intenational Searching Authority for the parent application (PCT/US2008/002364).
Notice of Reasons for Rejection in the related application in Japan (Japanese Patent Application No. 2009-550926), Mar. 15, 2012.

(Continued)

*Primary Examiner* — Avinash Savani
(74) *Attorney, Agent, or Firm* — Timothy S. Stevens

(57) ABSTRACT

A chemical analysis method for determining the concentration of carbon monoxide, gaseous water and gaseous hydrocarbon in a combustion gas. The method includes the following steps: (a) directing wavelength modulated light from a single tunable diode laser at a wavelength in the range of from 2 to 2.5 micrometers through the combustion gas to a light detector to produce an absorption profile of the combustion gas (b) digitizing the adsorption profile of the combustion gas; (c) storing the digitized adsorption profile in a digital computer; (d) processing the digitized adsorption profile in the digital computer to produce an output from the computer indicative of the concentration of carbon monoxide, gaseous water and gaseous hydrocarbon in the combustion gas.

11 Claims, 11 Drawing Sheets

OTHER PUBLICATIONS

Lackner, et al., In situ laser measurements . . . single fuel particle, Measurement Science and Technology, Oct. 2002, vol. 13, No. 10, pp. 1545-1551.

Wang, et al., In situ combustion . . . near 2.3 microns, 38th Aerospace Sciences Meeting & Exhibit, Feb. 16, 2000, AIAA 2000-0255, pp. 1-8.

Extended European search report in related application hereto in the EPO (EP 08 72 5953), Feb. 9, 2010.

Wu et al., Tunable Diode Laser Measurements of Co . . . and Enerby Efficiency; Metallurgical and Materials Transactions B, vol. 36B, Feb. 2005, pp. 53-57.

Louvet et al., Automotive exhaust gas analysis by . . . spectroscopy; SPIE vol. 3108, 1997, pp. 54-62.

Teichert et al., Simultaneous in situ measurement of Co . . . diode lasers; Applied Optics, Apr. 20, 2003, vol. 42, No. 12, pp. 2043-2051.

Mihalcea et al., Advanced Diode Laser . . . and Gas Temperature; 27th Symposium (International) on Combustion/The Combustion Institute, 1995, pp. 95-101.

First Office Action from the State Intellectual Property Office of the Peoples Republic of China in the related application in China, Dec. 1, 2010.

European Patent Office notice of intention to grant the European patent corresponding to the instant application, including the allowed claims, Jun. 12, 2012.

\* cited by examiner

COMBUSTION GAS ANALYSIS

This application claims priority to U.S. Provisional Patent Application No. 60/903,495 filed Feb. 26, 2007 and is a continuation of PCT Application No. PCT/US2008/002364 filed Feb. 22, 2008. The instant invention is in the field of combustion gas analysis and more specifically the instant invention is in the field of tunable diode laser spectroscopic analysis of combustion gases. Tunable diode laser spectroscopic analysis of combustion gases is known and described in the prior art, for example, by: Lackner et al., Thermal Science, V.6, p 13-27, 2002; Allen, Measurement Science and Technology, V.9, p 545-562, 1998; Nikkary et al., Applied Optics, V.41(3), p 446-452, 2002; Upschulte et al., Applied Optics, V.38(9), p 1506-1512, 1999; Mihalcea et al., Measurement Science and Technology, V.9, p 327-338, 1998; Webber et al., Proceedings of the Combustion Institute, V.28, p 407-413, 2000; Ebert et al., Proceedings of the Combustion Institute, V.30, p 1611-1618, 2005; Nagali et al., Applied Optics, V.35(21), p 4027-4032, 1996; and U.S. Pat. Nos. 7,248,755 7,244936 and 7,217,121.

BACKGROUND OF THE INVENTION

Despite the significant advances in the prior art, problems related to poor sensitivity, background interferences and temperature interferences remain as significant problems for the application of tunable diode laser spectroscopic simultaneous analysis of combustion gas for carbon monoxide, gaseous water and gaseous hydrocarbon.

SUMMARY OF THE INVENTION

The instant invention is a solution to the above-stated problems for the simultaneous analysis of carbon monoxide, gaseous water and gaseous hydrocarbon in combustion gas by tunable diode laser spectroscopy. The sensitivity of analysis is improved by operating the tunable diode laser in a wavelength range of from 2 to 2.5 micrometers. Multivariate processing techniques for manipulating the spectral data allow the simultaneous determination of carbon monoxide, gaseous water and gaseous hydrocarbon even though only a single tunable diode laser is used. More specifically, the instant invention is a chemical analysis method for determining the concentration of carbon monoxide, gaseous water and gaseous hydrocarbon in a combustion gas, comprising the steps of: (a) directing wavelength modulated light from a single tunable diode laser at a wavelength in the range of from 2 to 2.5 micrometers through the combustion gas to a light detector to produce an absorption profile of the combustion gas (b) digitizing the adsorption profile of the combustion gas; (c) storing the digitized adsorption profile in a digital computer; (d) processing the digitized adsorption profile in the digital computer to produce an output from the computer indicative of the concentration of carbon monoxide, gaseous water and gaseous hydrocarbon in the combustion gas.

In a related embodiment, the instant invention is a method for monitoring and controlling a combustion driven thermal processing system to meet efficiency, environmental and operational safety goals, the combustion driven thermal processing system producing a combustion gas, comprising the steps of: (a) determining the concentration of oxygen in the combustion gas; (b) determining the temperature of the combustion gas; and (c) determining the concentration of carbon monoxide, gaseous water and gaseous hydrocarbon in a combustion gas, by a method comprising the steps of: (i) directing wavelength modulated light from a single tunable diode laser at a wavelength in the range of from 2 to 3 micrometers through the combustion gas to a single light detector to produce an absorption profile of the combustion gas; (ii) digitizing the adsorption profile of the combustion gas; (iii) storing the digitized adsorption profile in a digital computer; (iv) processing the digitized adsorption profile in the digital computer to produce an output from the computer indicative of the concentration of carbon monoxide, gaseous water and gaseous hydrocarbon in the combustion gas.

DETAILED DESCRIPTION

The measurement of gas species in a combustion system is important for safe, environmentally responsible, and efficient operation. While not limited thereto, the instant invention has particular importance to hydrocarbon processing furnaces and heaters.

The specific gas species and condition measurements used in this invention are, Oxygen ($O_2$), Carbon Monoxide (CO), Combustion Gas Temperature, Water ($H_2O$) and hydrocarbons (C—H) such as methane ($CH_4$).

Figure 1:
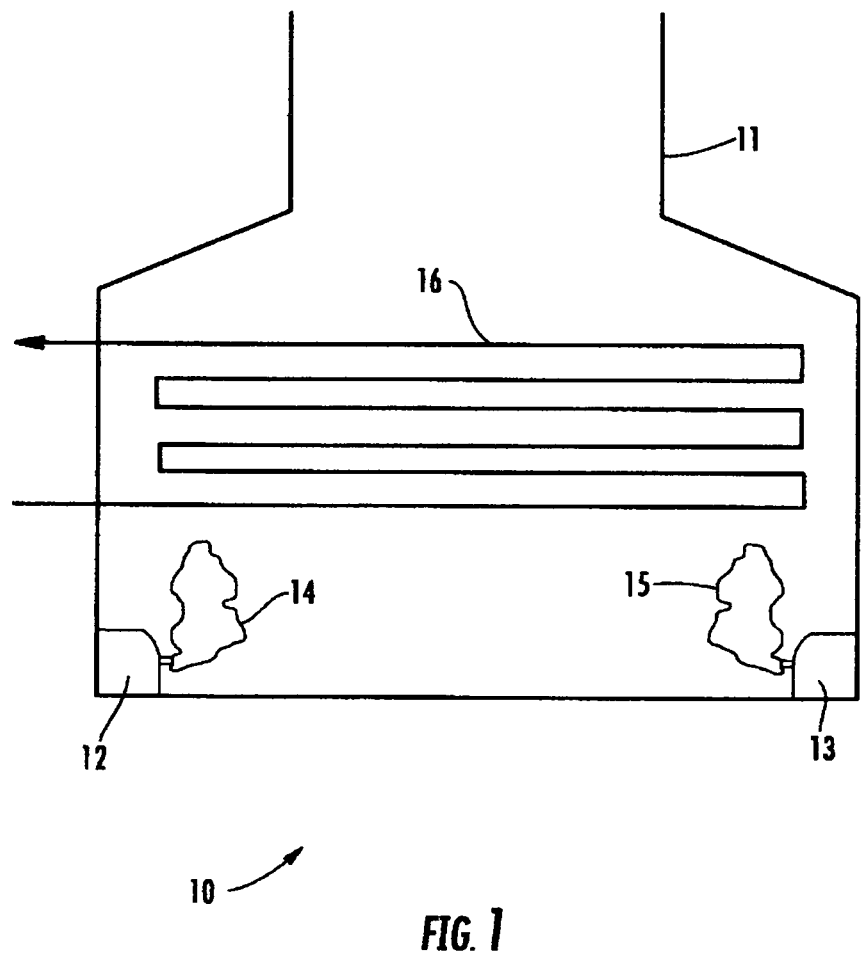
FIG. 1 is a schematic drawing of a hydrocarbon processing heater or furnace.

Referring now to FIG. 1, therein is shown schematic drawing of a hydrocarbon processing heater or furnace 10 such as an ethylene cracker, a petroleum refinery heater, a petroleum refinery hydrocracker, a petroleum refinery fluidized catalytic cracker and an electrical power generation steam boiler. The heater or furnace 10 is comprised of an enclosure or wall 11, a pipe 16 carrying, for example, a stream of hydrocarbon to be heated, by the flames 14 and 15 from burners 12 and 13.

Figure 2:
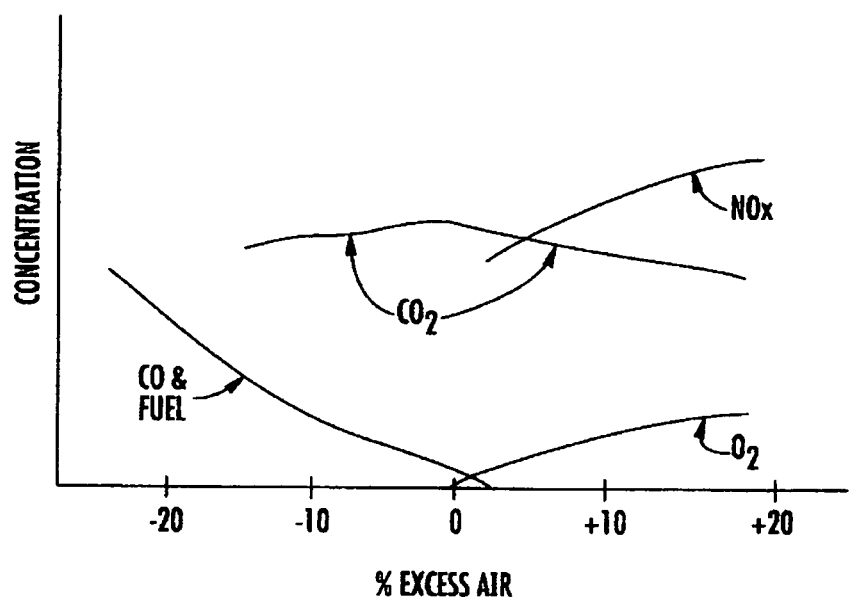
FIG. 2 shows the relationship between key combustion parameters for the heater or furnace of FIG. 1.

Referring now to FIG. 2, therein is shown a plot of concentration v. percent excess burner air for the relationship between key combustion parameters for the heater or furnace of FIG. 1. The primary operational concerns addressed by the instant invention are, efficiency of the burners (optimum air/fuel ratio), emissions from the combustion system (CO, $CO_2$, NOx, etc.), and safety monitoring (flame loss, fuel rich burner conditions, leak or rupture of the product tube).

Combustion efficiency requirements can be generally summarized as optimizing the air/fuel ratio to the burners with the lowest amount of excess air in the combustion by-products. Fuel feed to the burners is typically determined by the firing rate required for processing (amount of heat required). Air feed to the burners must be high enough to allow complete combustion without the production of excess emissions (CO, etc.) and unburnt fuel (hydrocarbons). Excess air will be heated by the flame, consuming some of the heat which then is not available for the primary purpose of the combustion system (such as cracking feedstock). Excess air to a burner will also generate NOx emissions. FIG. 2 illustrates the relationship between efficiency, safety and emissions.

Emissions requirements are determined by the operator or the governmental authority. In many cases an industrial plant or the individual furnace/heater has a limit on the amount of pollutants and greenhouse gases that can be emitted. Primary pollutants are carbon monoxide (CO), NOx (nitric oxide+ nitrogen dioxide) and carbon dioxide ($CO_2$). In some cases the firing rate of the burners (production rate) can be limited by the need to remain below mandated emissions limits. Measurement of the pollutants, or the conditions required to generate the pollutants can be used to control and reduce emissions reduction.

Safe operation of combustion systems requires that explosive mixtures are not present in the combustion system. These explosive mixtures can occur under three common conditions. First, if the burner(s) are not supplied with enough air, unburnt fuel will be present in the burner(s). This unburnt fuel can be ignited if excess air is then introduced into the system, from the burner air feed or from air leaks into the system. Second, if the burner(s) flame goes out (flameout, liftoff) the air/fuel feed to the burner will enter the combustion chamber, any subsequent ignition source can ignite this mixture. Third, if the furnace/heater is used for processing hydrocarbons, a leak in the product tube can introduce unburnt hydrocarbons to the combustion chamber. If excess air is present, along with an ignition source an explosion can occur. Measurement of the presence of the explosive mixture along with other conditions can both indicate the un-safe condition and the source of the safety breach.

Figure 3A:
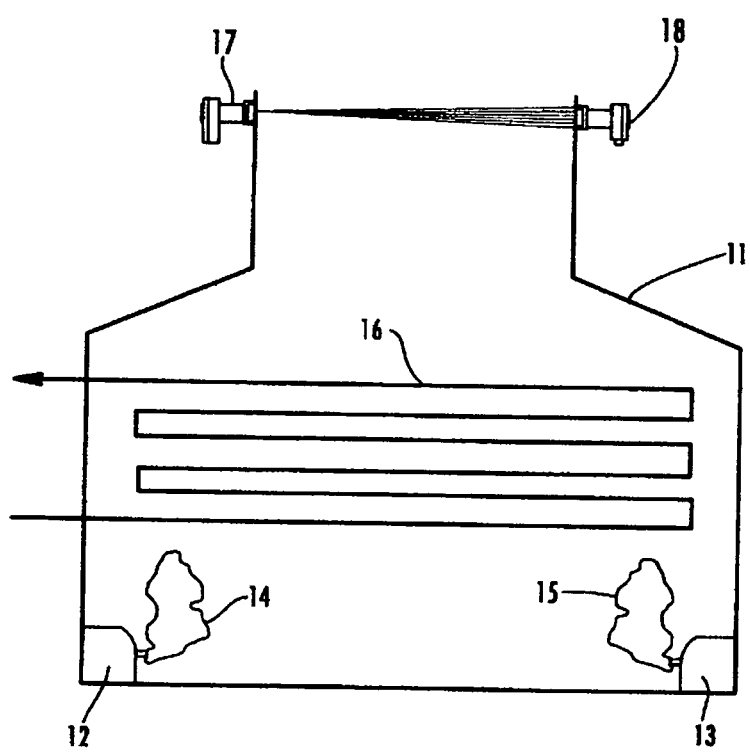
FIG. 3a is a schematic drawing of the heater or furnace of FIG. 1 employing a tunable diode laser gas analysis system.
Figure 4:
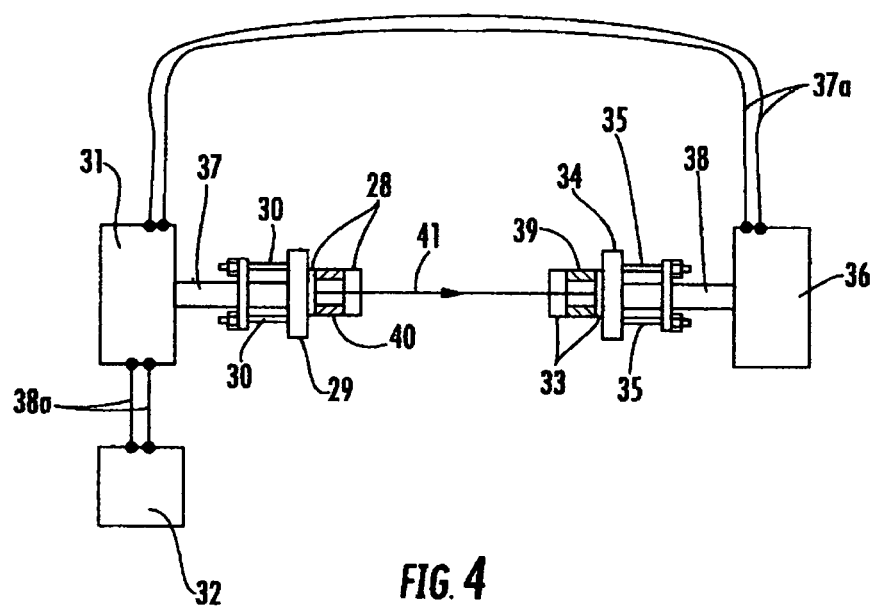
FIG. 4 is a more detailed drawing of the tunable diode laser gas analysis system.

Referring now to FIG. 3a, therein is shown a schematic drawing of the heater or furnace of FIG. 1 employing a tunable diode laser gas analysis system comprising a tunable diode laser sending unit 17 and a detector 18. Referring now to FIG. 4, therein is shown a more detailed drawing of the tunable diode laser gas analysis system. The tunable diode laser gas analysis system includes a laser module 37 containing the tunable diode laser. A control unit 31 contains the central processing unit programmed for signal processing (to be discussed below in greater detail) as well as the temperature and current control for the tunable diode laser and a user interface and display. Alignment plate 29 and adjustment rods 30 allow alignment of the laser beam 41. Dual process isolation windows 28 are mounted in a four inch pipe flange 40. The space between the windows 28 is purged with approximately 25 Liters per minute of nitrogen at ten pounds per square inch gauge pressure. The flange 40 is mounted through the wall of the furnace.

Referring still to FIG. 4, the laser beam 41 is passed through the combustion gas and then through dual process isolation windows 33 to a near infrared light detector 38. The windows 33 are mounted in a four inch pipe flange 39. The space between the windows 33 is purged with approximately 25 Liters per minute of nitrogen at ten pounds per square inch gauge pressure. The flange 39 is mounted through the wall of the furnace. Alignment plate 34 and adjustment rods 35 allow alignment of the detector optics with the laser beam 41. Detector electronics 36 are in electrical communication with the control unit 31 by way of cable 37a. The control unit 31 is also in electrical communication (by way of electrical cables 38a) with a process control system 32 for controlling the furnace 10. The system shown in FIG. 4 is commercially available from Analytical Specialties of Houston, Tex.

The system shown in FIG. 4 operates by measuring the amount of laser light at specific wavelengths, which light is absorbed (lost) as it travels through the combustion gas. Carbon monoxide, gaseous water and hydrocarbons each have a spectral absorption of infrared light that exhibits unique fine structure. The individual features of the spectra are seen at the high resolution of the tunable diode laser 37.

Figure 3B:
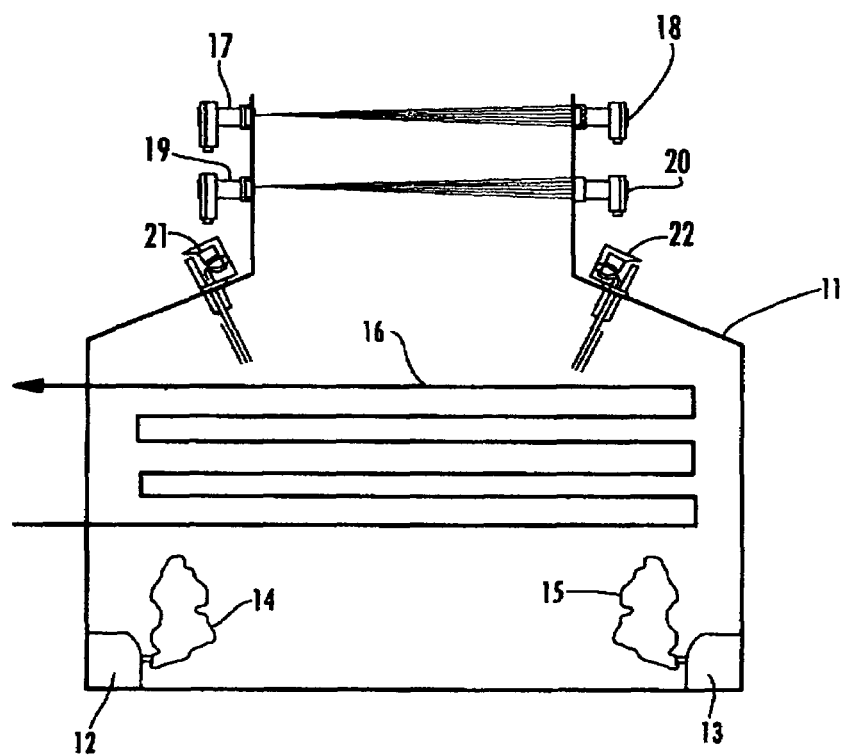
FIG. 3b is a schematic drawing of the heater or furnace of FIG. 1 employing two tunable diode laser gas analysis systems and a pair of zirconia oxygen sensors.

Referring now to FIG. 3b, therein is shown a schematic drawing of the heater or furnace of FIG. 1 employing two tunable diode laser gas analysis systems 17, 18, 19 and 20, and a pair of zirconia oxygen sensors 21 and 22. The system shown in FIG. 3b is a preferred embodiment of the instant invention. The oxygen measurement can be performed a number of ways. Two common methods are zirconia oxide probes, tunable diode laser (TDL) spectroscopy, or a combination of both. This application will include a description of a combination of zirconia oxide probes with tunable diode laser spectroscopy in relation to FIG. 3b. The TDL oxygen analyzer 19, 20 at a wavelength in the range of from 759 to 779 nanometers provides a path average oxygen concentration to avoid errors due to the uneven oxygen distribution across the firebox. By measuring two oxygen absorption peaks, Gas Temperature can be calculated and provided as an output from the analyzer. The zirconia oxygen probes provide a point measurement of oxygen which can be used to diagnose localized inefficiencies in multi-burner systems.

CO measurement is also possible using a number of analysis methods such as, solid state sensors, non dispersive infrared and tunable diode laser. The preferred embodiment of this invention is the use of TDL spectroscopy to measure the CO in the combustion gas. With proper absorption line selection in the wavelength range of from 2 to 2.5 micrometers it is also possible to measure $H_2O$ and hydrocarbons (methane and others) with a single tunable diode laser system. It is also possible to use multiple lasers to provide single species measurement per laser or combinations of single and multiple species measurements per laser.

Referring still to FIG. 3b two individual diode lasers systems 17, 18, 19 and 20 are used to provide measurements of, $O_2$, CO, $H_2O$, gas temperature, and unburnt hydrocarbons including but not limited to methane (CH4). TDL is an optical measurement. The measured gas absorbs the laser light at a specific wavelength. The amount of light absorbed is a function of gas concentration, pressure, temperature and optical path length. The process heater/furnace also has single or multiple burners 12 and 13, that are used to provide the heat for the thermal processing. These burners are supplied with air and fuel, both of which are controlled to provide the desired heat, control efficiency, reduce emissions and ensure safe operation. There are a number of potential operating conditions, some of which will be outlined below, where the gas species measurements may be used to meet the goals of maximum heat capacity, efficient operation (lowest burner fuel costs), safe operation (avoiding explosive mixtures in the furnace), and reducing emissions.

Referring still to FIG. 3b, under normal operating conditions where the burners 12 and 13 are lit and the product being processed is contained in the product tube 16, the key operational parameter is minimizing excess air, while providing the desired heat, minimizing unburnt fuel, and staying within emissions limits. The gas measurements listed above may be used as follows. Oxygen and CO measurements will indicate the efficiency of the burner(s), minimum oxygen concentration without significant levels of CO can indicate optimum overall furnace fuel efficiency. The combination of path average and point source oxygen measurements can indicate localized burner efficiency if multiple burners are present in the system. Gas temperature measurement can indicate the amount of heat available for product processing. CO can also be used as a pre-cursor to fuel rich conditions where burner fuel (combustibles) is not burned and present in the combustion chamber. C—H measurement can be used to indicate the presence of unburnt fuel from the burners. $H_2O$ measurement can be used to calculate efficiency. A combination of oxygen and CO measurement can be used to predict or calculate the pollutant emissions such as $CO_2$ and NOx since both of these pollutants increase as air and fuel levels to the burners increase. For example NOx is produced from the nitrogen and oxygen present in the air supplied to the burner(s), increased excess air (above the minimum level required) will lead to increased NOx formation.

Under conditions produced by a burner flame loss or flameout, the gas measurements may be used as follows. Oxygen levels will rise since oxygen present in the burner air feed is not being consumed by the combustion process. Gas temperature levels will fall rapidly upon the loss of the heat source (flame). Gas $H_2O$ levels will fall rapidly since they are produced as a combustion by product. Methane and other hydrocarbon levels will increase in large amounts. By providing and monitoring each of these gas measurements a loss of burner flame can be inferred.

Under conditions produced by a product tube leak, where the product tube contains hydrocarbons, the following conditions may be monitored. Hydrocarbon levels will increase in the combustion chamber as the product from the tube enters the combustion chamber. If steam is also present in the product tube, $H_2O$ levels will increase as the steam enters the combustion chamber. Oxygen levels, gas temperature and CO levels may also change under these conditions and potentially be used for diagnostics and control.

Under conditions produced by a product tube leak, where the product tube contains steam but no hydrocarbons, the following conditions may be monitored. $H_2O$ levels will increase as the steam enters the combustion chamber. Oxygen levels, gas temperature and CO levels may also change under these conditions and potentially be used for diagnostics and control.

The preferred embodiment of this invention uses tunable diode laser spectrometer(s) to measure oxygen, carbon monoxide, hydrocarbons such as methane, water vapor and temperature. These measurements can be utilized in many combustion driven thermal processing systems, one example being refinery process heaters.

TDL spectroscopy uses a tunable diode laser as the light source. This laser is typically controlled at a constant temperature to establish the course wavelength position, the laser is then modulated using a current ramp from the control electronics, modulation results in a wavelength scan over a repeated range (i.e. 760 nm to 761 nm for oxygen). The modulated laser light passes through beam shaping optics, and then a first process isolation window, through the gas being measured where if the gas being measured is present it absorbs a portion of the infrared light transmitted across the process, another process isolation window, to an appropriate light sensitive detector selected for the wavelength being used for measurement. The detector signal is sampled by an appropriate data acquisition system, the results are then processed by the analyzer digital central processing unit (CPU). One example of such a device is the TruePeak Tunable Diode Laser analyzer available from Analytical Specialties, Inc of Houston, Tex.

Figure 5:
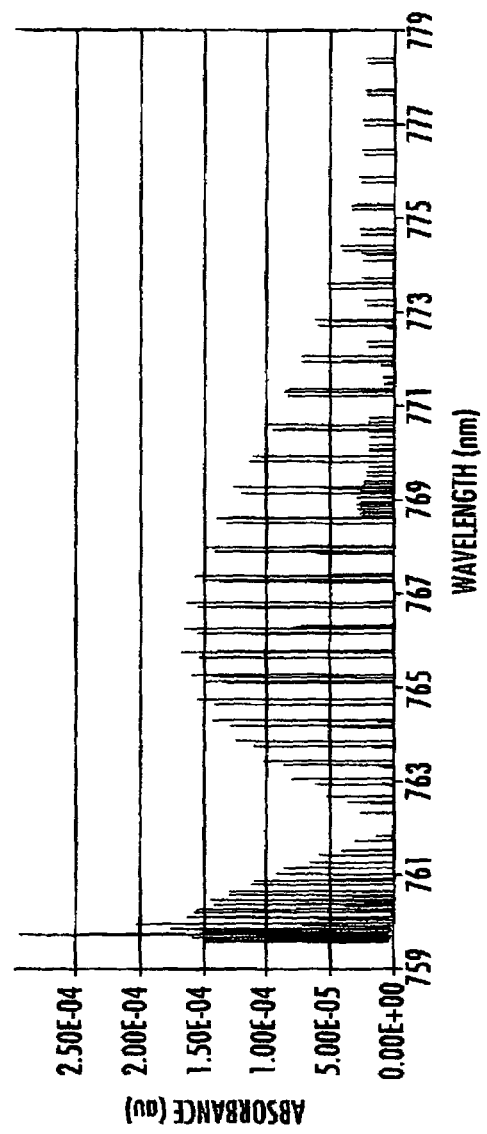
FIG. 5 shows the infrared spectrum for oxygen in the 759 to 779 nm wavelength region.

Each of the gases used for measurement have a unique absorption of infrared light. One example of this is shown in FIG. 5, this is the infrared absorption spectra for oxygen. By selecting one or more of the specific absorption peaks, inputting the distance the laser light transmits across the process along with gas temperature and pressure, a path average concentration can be calculated and reported. This path average concentration basically counts the number of molecules of the gas being measured that are in the beam of laser light. One advantage of a path average measurement versus a point source measurement (as with zirconia oxygen sensors) is that all of the analyte is measured, point sensors only measure a small portion of the process, if the analyte is distributed throughout the process a point measurement may not be representative of the entire system. In some cases both a path average and one or more point source measurements may be desirable, for example to diagnose burner malfunctions. If path and point measurements are desired a combination of both types of measurements may be employed as shown in FIG. 3b.

Oxygen measurement can be made with this type of analytical device by selecting any suitable absorption peak shown in FIG. 5, from 759 to 779 nm.

It is also possible to infer the gas temperature by scanning the laser over two suitable oxygen peaks, for example 760.55 nm and 760.56 nm. The oxygen absorption peak strength is strongly related to the gas temperature, if two lines are selected that have sufficiently different line strength vs. temperature, measuring both and comparing the line strength allows the inference of gas temperature. This same approach may be used with other analytes (moisture as an example), this embodiment uses the oxygen peaks for temperature measurement.

Figure 6:
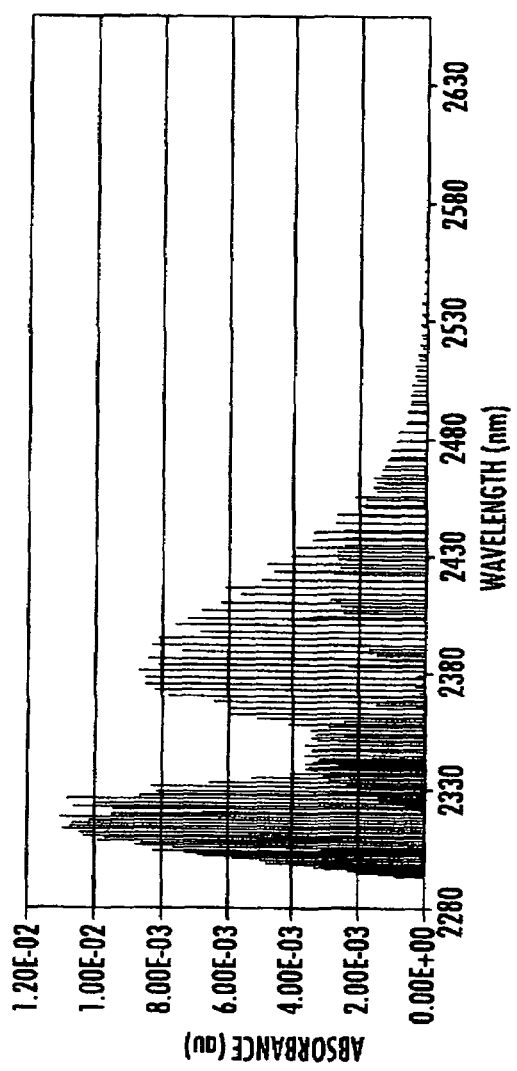
FIG. 6 shows the infrared spectrum for carbon monoxide in the 2280 to 2630 nm wavelength region.
Figure 7:
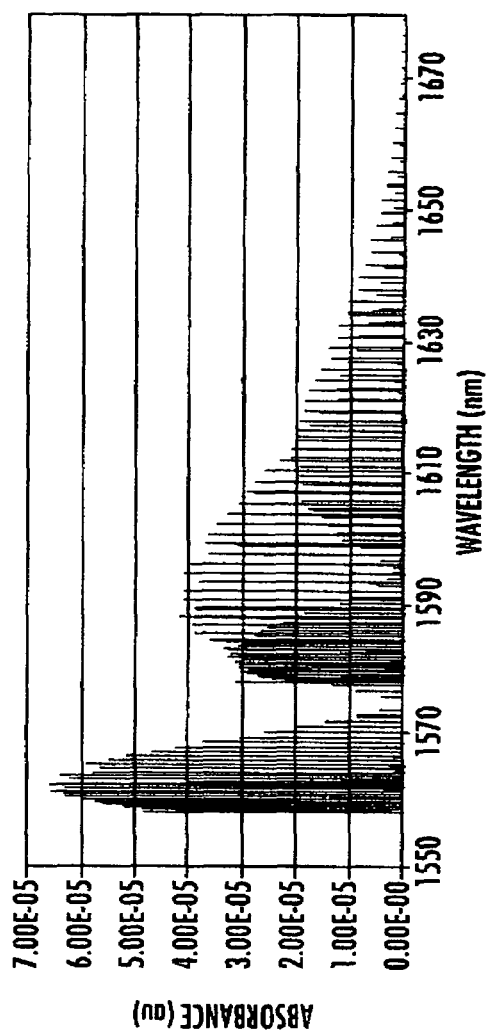
FIG. 7 shows the infrared spectrum for carbon monoxide in the 1550 to 1680 nm wavelength region.

Measurement of carbon monoxide (CO) is performed in a similar method. FIGS. 6 & 7 show the absorbing CO peaks at two different wavelength regions. Depending on the sensitivity requirements for the CO measurement and the cost of the diode laser either wavelength region may be selected.

The preferred embodiment of this invention uses the CO peaks in the wavelength range of 2290 to 2580 nm. Two specific examples will be outlined as they are particularly well suited for combustion analysis requirements at high temperatures. Measurement of CO close to the burners themselves has an advantage in that the CO levels are typically higher closest to the burners, making the measurement and control simpler. As the combustion gases travel further from the burner system they continue to react, this reaction results in lower CO levels further from the burner(s) at lower temperature zones. In addition the measurement response time is reduced.

Figure 8:
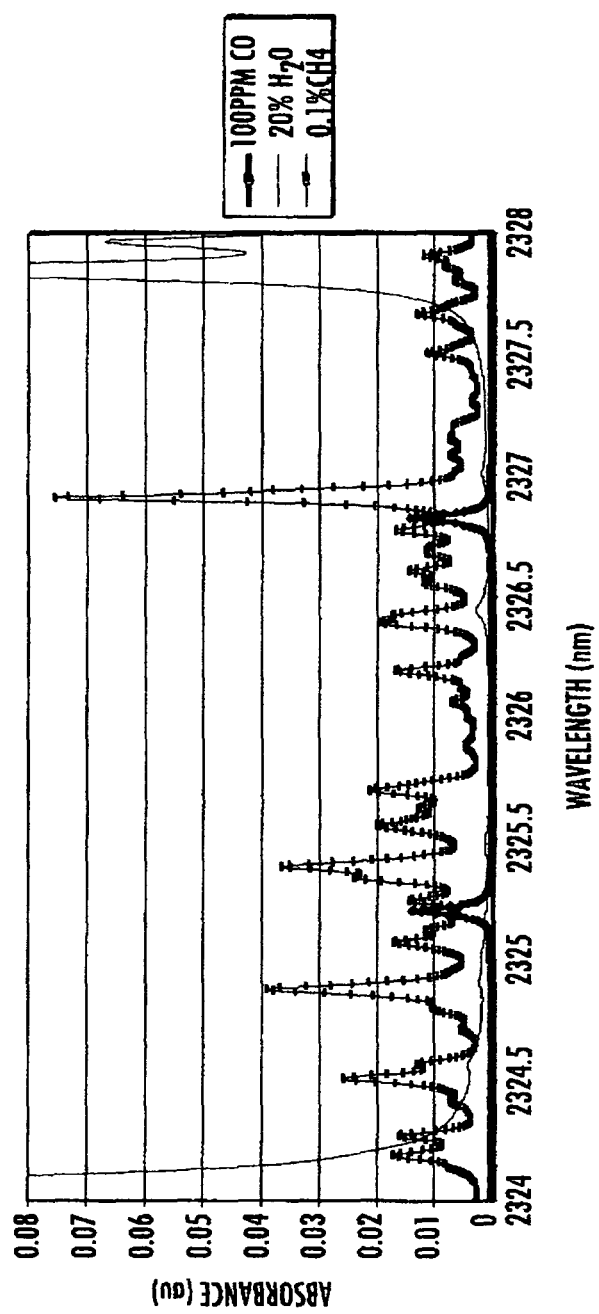
FIG. 8 shows HITRAN spectra of CO, $H_2O$ and CH4 from 2324 to 2328 nm.

FIG. 8 shows HITRAN absorption spectra of CO, $H_2O$ and CH4 from 2324 to 2328 nm. This wavelength region is one example where a single diode laser can be wavelength modulated to cover the absorption wavelengths for CO, $H_2O$ and multiple hydrocarbons, methane being the example used here.

Figure 9:
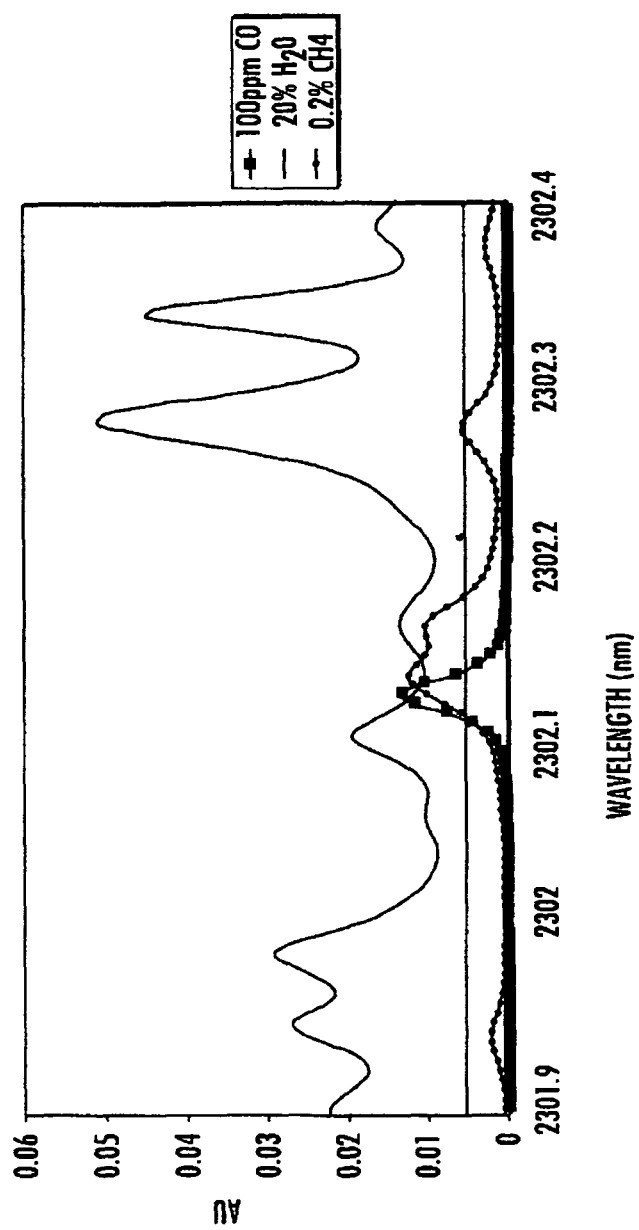
FIG. 9 shows HITRAN spectra of CO, $H_2O$ and CH4 from 2301.9 to 2302.4 nm.

FIG. 9 shows HITRAN absorption spectra of CO, $H_2O$ and CH4 from 2301.9 to 2302.4 nm. This wavelength region is another example where a single diode laser can be wavelength modulated to cover the absorption wavelengths for CO, $H_2O$ and multiple hydrocarbons, methane being the example used here.

Figure 10:
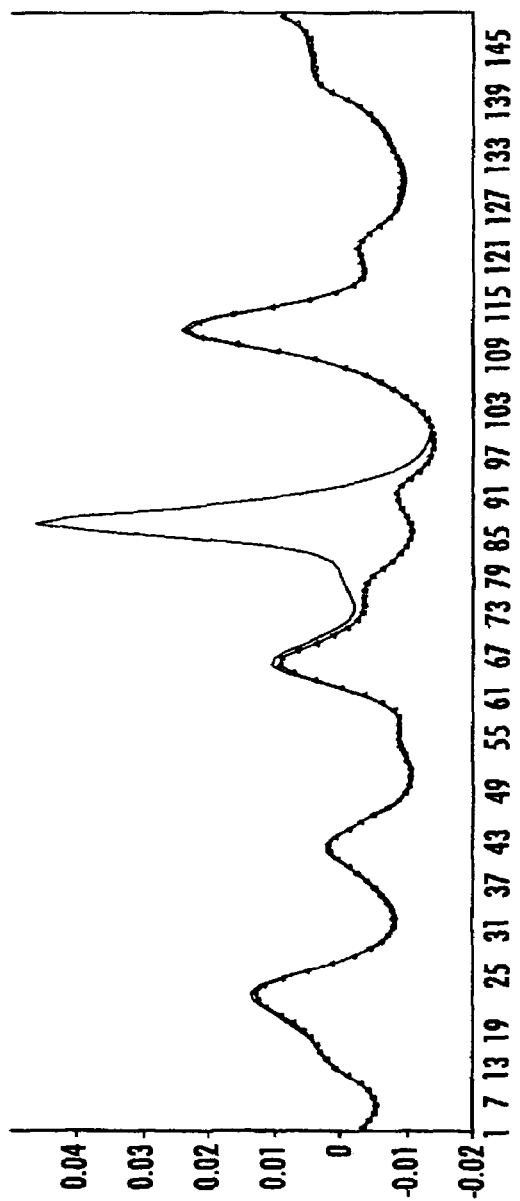
FIG. 10 shows absorption spectra of CO and $H_2O$ collected across a long path at 1,100° C.

FIG. 10 shows absorption spectra, collected across a long path at 1100C, in approximately the same wavelength range as FIG. 9 (2301.9 to 2302.4 nm) wherein the plain curve relates to CO plus $H_2O$ while the triangle marked curve relates to $H_2O$. As can be seen by comparing standard HIT- RAN spectra with the measured spectra from a operating furnace, the background H2O absorption pattern is different than expected. This is primarily due to the fact that HITRAN was originally designed for atmospheric monitoring applications and it isn't very accurate for high temperature conditions. Because of long path (20 meters), background H2O absorbance interference with CO absorbance is significant. Concentration prediction based on a simple peak height measurement or peak area integration is not possible (or at least very difficult) while maintaining measurement integrity.

CLS (classical least squares) signal processing is a preferred solution to this problem in the instant invention. Preferably, the signal processing is done by a digital computer, preferably a general purpose digital computer programmed to perform one of the following types of analysis of the signal(s) stored in the digital computer. CLS is a type of multivariate analysis which uses a mathematical model to predict concentration level of each component. Multivariate analysis includes classical least square (CLS), principal components regression (PCR) and partial least squares (PLS). CLS is probably the simplest. It requires calibration to get all the spectra of each component, and then build a mathematical model for future mixture measurement. Calibration is the process of constructing a mathematical model to relate the output of an instrument to properties of samples. Prediction is the process of using the model to predict properties of a sample given an instrument output. For example, the absorbance at a given wavelength can be related to the concentration of an analyte. To construct the model, instrument responses from samples with known concentration levels are measured and a mathematical relationship is estimated which relates the instrument response to the concentration of a chemical component(s). This model may be used to predict the concentration of a chemical component in future samples using the measured instrument response(s) from those samples. Many instrumental responses can be considered, and a number of sample properties can be predicted. In many applications, one response from an instrument is related to the concentration of a single chemical component. This is referred to as univariate calibration because only one instrument response is used per sample. Multivariate calibration is the process of relating multiple responses from an instrument to a property or properties of a sample. The samples could be, for example, a mixture of chemical components in a process stream, and the goal is to predict the concentration levels of the different chemical components in the stream from infrared measurements.

Scanning the laser wavelength across individual absorption peaks for CO, $H_2O$ and specific hydrocarbons such as CH4, allows the measurement and reporting of these components. Multivariate models may be required and used to enhance the measurement. The following specific wavelengths (in nanometers) are specifically recommended when the combustion gas has a temperature of about 1,100° C.: 2302.1; 2303.9; 2319.1; 2323.6; 2325.2; 2326.8; 2331.9; 2333.7; 2335.5; 2342.8; 2346.8; 2348.2; 2356.1; 2363.1; and 2373.1. The following specific wavelengths (in nanometers) are specifically recommended when the combustion gas has a temperature of about 300° C.: 2307.8; 2320.6; 2323.6; 2331.9; 2339.3; 2353.9; 2360.8; 2368.0; 2373.1; 2389.3; and 2401.0. Thus, there are a number of possible wavelengths that permit the simultaneous determination of CO, $H_2O$ and hydrocarbon (such as $CH_4$). The selection of the best wavelength is application dependent and determined by a reasonable degree of experimentation. Factors such as the desired sensitivity, the optical pathlength (furnace size) and combustion gas temperature are important variables.

The central feature of the preferred embodiment of the instant invention is the monitoring of oxygen, temperature, carbon monoxide, water vapor and/or hydrocarbons in a single analytical system. The combination of these measurements along with an understanding of the process conditions that affect these gas measurements allows not only combustion efficiency optimization, emissions reduction and safety monitoring, but also allows the discrimination between conditions. One embodiment of this invention allows discrimination between air rich or fuel rich conditions along with discrimination between unsafe conditions such as product tube leaks and burner flame out. Another embodiment of this invention which includes additional point oxygen measurements allows localized diagnostics in multiple burner systems.

CONCLUSION

In conclusion, it should be readily apparent that although the invention has been described above in relation with its preferred embodiments, it should be understood that the instant invention is not limited thereby but is intended to cover all alternatives, modifications and equivalents that are included within the scope of the invention as defined by the following claims.

What is claimed is:

1. A chemical analysis method for determining the concentration of carbon monoxide, gaseous water, oxygen and gaseous hydrocarbon in a combustion gas, comprising the steps of: (a) directing wavelength modulated light from a single tunable diode through beam shaping optics laser at a wavelength in the range of from 2 to 2.5 micrometers through the combustion gas to a light detector to produce an absorption profile of the combustion gas and performing an oxygen measurement using an oxygen analyzer (b) digitizing the absorption profile of the combustion gas; (c) storing the digitized absorption profile in a digital computer; (d) processing the digitized absorption profile in the digital computer to produce an output from the computer indicative of the concentration of carbon monoxide, gaseous water and gaseous hydrocarbon in the combustion gas.

2. The method of claim 1, wherein in step (d) the processing comprises multivariate analysis.

3. The method of claim 1, wherein the combustion gas is produced by a process selected from the group consisting of an ethylene cracker, a petroleum refinery heater, a petroleum refinery hydrocracker, a petroleum refinery fluidized catalytic cracker and an electrical power generation steam boiler.

4. A method for monitoring and controlling a combustion driven thermal processing system to meet efficiency, environmental and operational safety goals, the combustion driven thermal processing system producing a combustion gas, comprising the steps of: (a) determining the concentration of oxygen in the combustion gas; (b) determining the temperature of the combustion gas; and (c) determining the concentration of carbon monoxide, gaseous, oxygen water and gaseous hydrocarbon in a combustion gas, by a method comprising the steps of: (i) directing wavelength modulated light from a single tunable through beam shaping optics diode laser at a wavelength in the range of from 2 to 3 micrometers through the combustion gas to a single light detector to produce an absorption profile of the combustion gas and performing an oxygen measurement using an oxygen analyzer; (ii) digitizing the absorption profile of the combustion gas; (iii) storing the digitized absorption profile in a digital computer; (iv) processing the digitized absorption profile in the digital computer to produce an output from the computer indicative of the concentration of carbon monoxide, gaseous water and gaseous hydrocarbon in the combustion gas.

5. The method of claim 4, wherein the concentration of oxygen in the combustion gas is determined using one or more point source oxygen sensors.

6. The method of claim 4, wherein the concentration of oxygen in the combustion gas and the temperature of the combustion gas are determined spectroscopically.

7. The method of claim 4, the combustion gas is produced by a process selected from the group consisting of an ethylene cracker, a petroleum refinery heater, a petroleum refinery hydrocracker, a petroleum refinery fluidized catalytic cracker and an electrical power generation steam boiler.

8. The method of claim 4, wherein the combustion driven thermal processing system employs one or more hydrocarbon burners and wherein the determinations are used to control the air and fuel feed rates of the burners to improve efficiency and reduce emissions.

9. The method of claim 4, wherein the determinations are used to indicate an unsafe condition in the combustion system.

10. The method of claim 4, wherein the combustion driven thermal processing system employs a plurality of hydrocarbon burners and a process tube and wherein the determinations are used to determine a condition selected from the group consisting of whether one or more burners are rich, whether one or more burners has flamed out, and whether a process tube is leaking.

11. The method of claim 4, further comprising determining carbon monoxide in the combustion gas using a point source carbon monoxide sensor.

* * * * *